United States Patent [19]
Charbonneau

[11] Patent Number: 5,609,710
[45] Date of Patent: Mar. 11, 1997

[54] REDUCED ODOR FRAGRANCE SAMPLER

[75] Inventor: Jack W. Charbonneau, Somerset, Wis.

[73] Assignee: Minnesota Mining and Manufacturing Company, St. Paul, Minn.

[21] Appl. No.: 451,880

[22] Filed: May 26, 1995

Related U.S. Application Data

[60] Division of Ser. No. 65,643, May 21, 1993, Pat. No. 5,419,958, which is a continuation-in-part of Ser. No. 889,732, May 28, 1992, abandoned.

[51] Int. Cl.⁶ ............................................. B32B 31/00
[52] U.S. Cl. ...................... 156/276; 156/90; 427/202; 427/203; 427/208.8; 427/385.5; 427/395
[58] Field of Search ........................ 427/202, 203, 427/208.8, 214, 372.2, 385.5, 391, 395, 407.1; 156/276, 90

[56] References Cited

U.S. PATENT DOCUMENTS

| | | | |
|---|---|---|---|
| 3,516,941 | 6/1970 | Matson | 252/316 |
| 3,691,140 | 9/1972 | Silver | 260/78.5 |
| 4,487,801 | 12/1984 | Turnbull et al. | 428/313.5 |
| 4,493,869 | 1/1985 | Sweeny et al. | 428/201 |
| 4,751,934 | 6/1988 | Moir et al. | 132/79 |
| 4,769,264 | 9/1988 | Dreger | 428/40 |
| 4,848,378 | 7/1989 | Moir et al. | 132/319 |
| 4,876,136 | 10/1989 | Chang et al. | 428/130 |
| 4,878,775 | 11/1989 | Norbury et al. | 401/132 |
| 4,925,517 | 5/1990 | Charbonneau et al. | 156/276 |
| 4,988,557 | 1/1991 | Charbonneau | 428/204 |
| 5,192,386 | 3/1993 | Moir et al. | 156/268 |

FOREIGN PATENT DOCUMENTS

| | | |
|---|---|---|
| 0161091 | 11/1985 | European Pat. Off. . |
| 0188883 | 7/1986 | European Pat. Off. . |
| 0189656 | 8/1986 | European Pat. Off. . |
| 0367581 | 5/1990 | European Pat. Off. . |
| 0525530 | 7/1992 | European Pat. Off. . |

OTHER PUBLICATIONS

Abstract: Section Ch, Week 8641, Derwent Publications Ltd., London, GB;JP, A, 61 197 649 Sep. 1, 1986.

*Primary Examiner*—Patrick Ryan
*Assistant Examiner*—Marie R. Yamnitzky
*Attorney, Agent, or Firm*—Gary L. Griswold; Walter N. Kirn; Dale A. Bjorkman

[57] ABSTRACT

A sampler for delivery of microencapsulated liquid fragrance material is provided that comprises at least one treated paper sheet defining an enclosed cavity. The paper sheet is at least partially treated with a volatile containment treatment, wherein the volatile liquid containment treatment is water-stable and organic liquid capsule fill-stable. The enclosed cavity is substantially completely defined by treated portion(s) of the sheet. Microcapsules comprising microencapsulated organic liquid capsule fill are disposed within the cavity.

13 Claims, 6 Drawing Sheets

REDUCED ODOR FRAGRANCE SAMPLER

This application is a divisional application of U.S. Ser. No. 08/065,643, filed May 21, 1993, now U.S. Pat. No. 5,419,958, which is a continuation-in-part of U.S. Ser. No. 07/889,732, filed on May 28, 1992, now abandoned.

FIELD OF THE INVENTION

This invention relates to microencapsulated fragrance samplers. More particularly, this invention relates to microencapsulated fragrances provided in a special reduced odor delivery system.

BACKGROUND

Fragrance samplers comprising a microencapsulated fragrance and at least one binder layer between two surfaces are well known in the industry. These samplers have become a common vehicle for advertising perfumes and other fragrances through inserts in magazines and the like. Use of these fragrance samplers has become objectionable to some consumers because many samplers have a tendency to prematurely release some fragrance. This premature emission may be due to accidental breakage of some microcapsules during the handling of the inserts or the magazines themselves, or may be due to the presence of non-encapsulated fragrance in the sampling device.

U.S. Pat. No. 4,925,517 discloses the use of a base coating on a surface to be subsequently coated with a microcapsule-bearing layer. The base coating functions in part to control the rate and degree of penetration of liquid from the carrier for microcapsules into the underlying paper. Typically the base coating is softened by the carrier liquid of the capsule containing slurry as a means of controlling the bond strength within the sampling device. Preferred polymers to be used in the base coating are water-softenable or organic solvent soluble, as disclosed at column 5, lines 7–15.

U.S. Pat. No. 4,988,557 discloses a similar carrier activated base coating that is applied in a discontinuous pattern to provide separate areas of the sampler in which the capsules are ruptured when the piece is opened, as well as regions in which the microcapsules may be freely removed.

U.S. Pat. No. 4,876,136 to Chang, et. al. discloses a lipstick sampling device that is a three layered structure to deliver a small amount of lipstick to a potential customer. The construction comprises a carrier sheet, a window sheet and a cover sheet. The carrier sheet may be any film or sheet material, and is preferably paper that has an oleophobic impregnate or a barrier layer coated on one side. See column 3, lines 31–37 and column 5, lines 10–32.

U.S. Pat. No. 4,878,775 to Norbury, et. al. discloses a dry liquid applicator that is a support surface with a coating of relatively large microcapsules and with an overlay of a liquid permeable top protective layer. The bottom of the support surface is preferably not readily penetrated by the liquid in the capsules, and is preferably completely impermeable to the liquid. See column 2, lines 27–33.

SUMMARY OF THE INVENTION

A sampler for delivery of microencapsulated liquid fragrance material is provided that comprises at least one treated paper sheet defining an enclosed cavity. The paper sheet is at least partially treated with a volatile containment treatment, wherein the volatile liquid containment treatment is water-stable and organic liquid capsule fill-stable. The enclosed cavity is substantially completely defined by treated portion(s) of the sheet. Microcapsules comprising microencapsulated organic liquid capsule fill are disposed within the cavity.

For purposes of this invention, the volatile liquid containment treatment is considered water-stable or organic liquid capsule fill-stable if a piece of ordinary bond paper provided with this treatment shows no absorption of liquid into the paper after ten minutes of exposure to a drop of water and to a drop of organic liquid capsule fill placed by an ordinary medicine dropper on the treated side of the paper. The volatile liquid containment treatment is a polymeric solution or emulsion that may be coated on a paper sheet in a standard coating process in-line with the printing of ink on the paper, and will cure in-line to provide the desired containment properties.

The problem of unwanted escape of volatile liquid capsule fill material as experienced in the prior art is avoided by the use of a volatile liquid containment treatment on the paper forming the microcapsule-containing cavity. Detectable odor emitting from the sampler is substantially reduced in accordance with the present invention. The use of this containment treatment provides an economical sampler that can be prepared using conventional printing press equipment. The sampler can be presented in an attractive paper format that is acceptable to the consumer, the manufacturer, the advertiser and even to the person that does not desire to be exposed to the fragrance being presented in the sampler.

BRIEF DESCRIPTION OF THE DRAWING

FIGS. 5–12 are sequential representations of steps in preparing a preferred embodiment of the present invention, wherein FIGS. 5–9 and 11 are plan views and FIGS. 10 and 12 are cross-sectional views of the embodiments shown in FIGS. 9 and 11, respectively.

DETAILED DESCRIPTION OF THE PRESENTLY PREFERRED EMBODIMENTS

In the description which follows, it will be assumed that the microcapsules contain a fragrance oil. However, it will be appreciated that other volatile microencapsulated liquids may be delivered in the same manner, and similarly prevented from unwanted leakage from the sampler that may cause olfactory discomfort or inconvenience. Examples of such materials include mineral oil microcapsules with associated pigments which have been used in samplers for eyeshadow and other cosmetic materials.

An additional benefit that may be realized in utilizing the volatile liquid containment treatment as described herein is the ability to print ink under the treatment, thus providing artwork in all areas of the sampler without fear of smearing of ink. The present volatile liquid containment treatment allows application of microcapsule slurries or anchoring layers that are cast from water over water-sensitive inks.

Similarly, this treatment allows the use of solvent sensitive inks directly under a coating of solvent-containing microcapsules without fear of smearing of the ink when the microcapsules are fractured.

Figure 1:
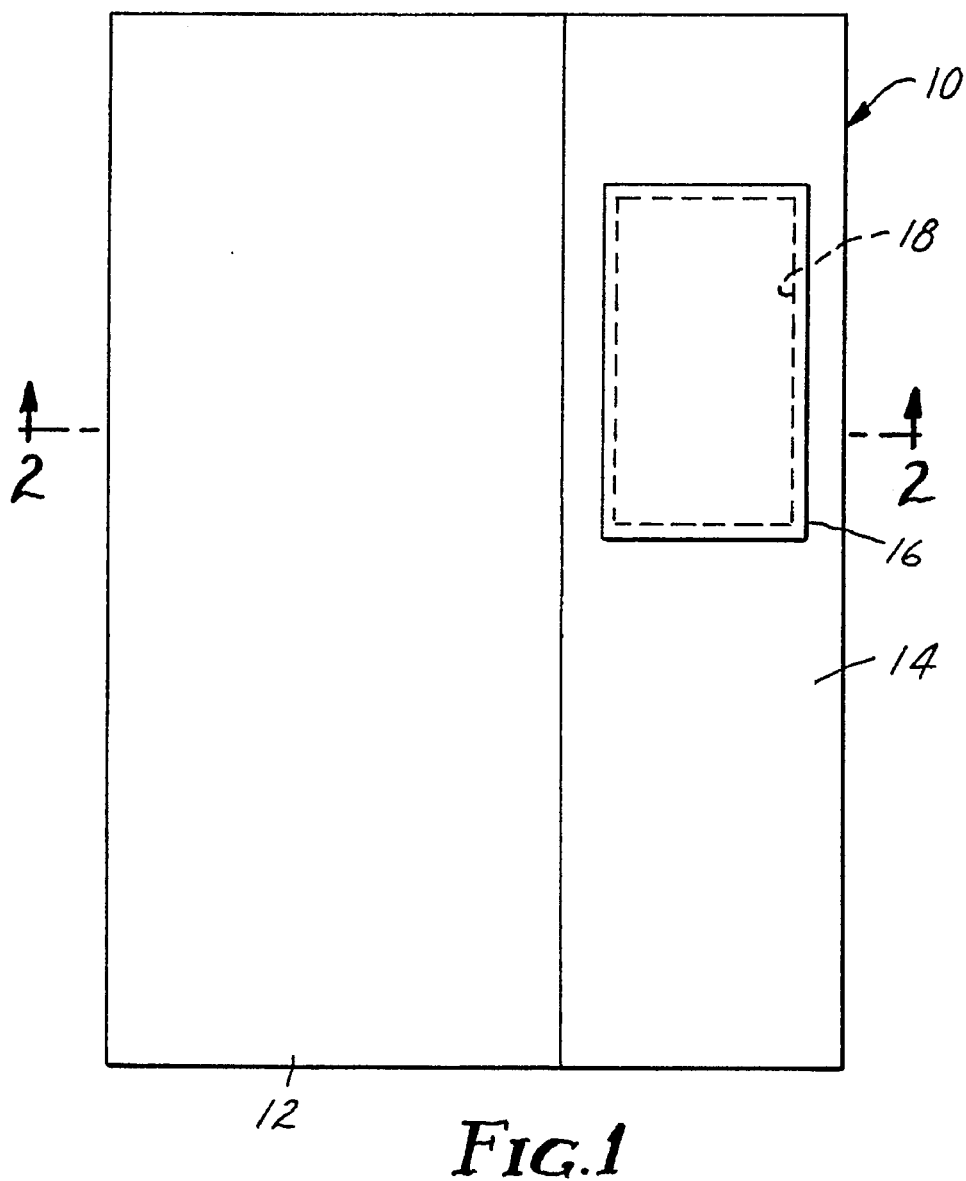
FIG. 1 is a plan view of an embodiment of the present invention, with the adhesive defining the cavity shown in phantom.

Turning now to the drawing, FIG. 1 is a plan view of embodiment 10 of the present invention. Paper substrate 12 is provided with a coating of volatile liquid containment treatment 14 at a portion of the substrate. Paper cover sheet 16 is adhered to paper substrate 12 by adhesive 18, shown in phantom.

Figure 2:
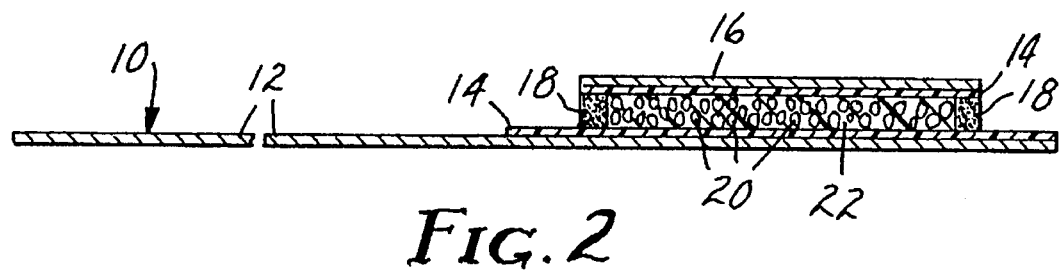
FIG. 2 is an enlarged cross-sectional view of the embodiment shown in FIG. 1 taken along line 2—2.

FIG. 2 is a cross sectional view of the embodiment 10 shown in FIG. 1 taken along line 2—2. Paper cover sheet 16 is adhered to paper substrate 12 by adhesive 18, thereby defining a cavity having microcapsules 20 disposed therein. The cavity may be described as being substantially defined by the treated paper, because the walls of the cavity are formed by treated paper and, at one small margin, adhesive. It is contemplated that small amounts of untreated paper may form a portion of the wall of the cavity if the adhesive does not overlie the volatile liquid containment treatment, but rather is adjacent to the treatment. Such an embodiment may be preferred where the volatile liquid containment treatment is found to unattractively peel upon separation of the cover paper from the substrate paper sheet. Microcapsules 20 are optionally bound to paper substrate 12 by binder 22.

Figure 3:
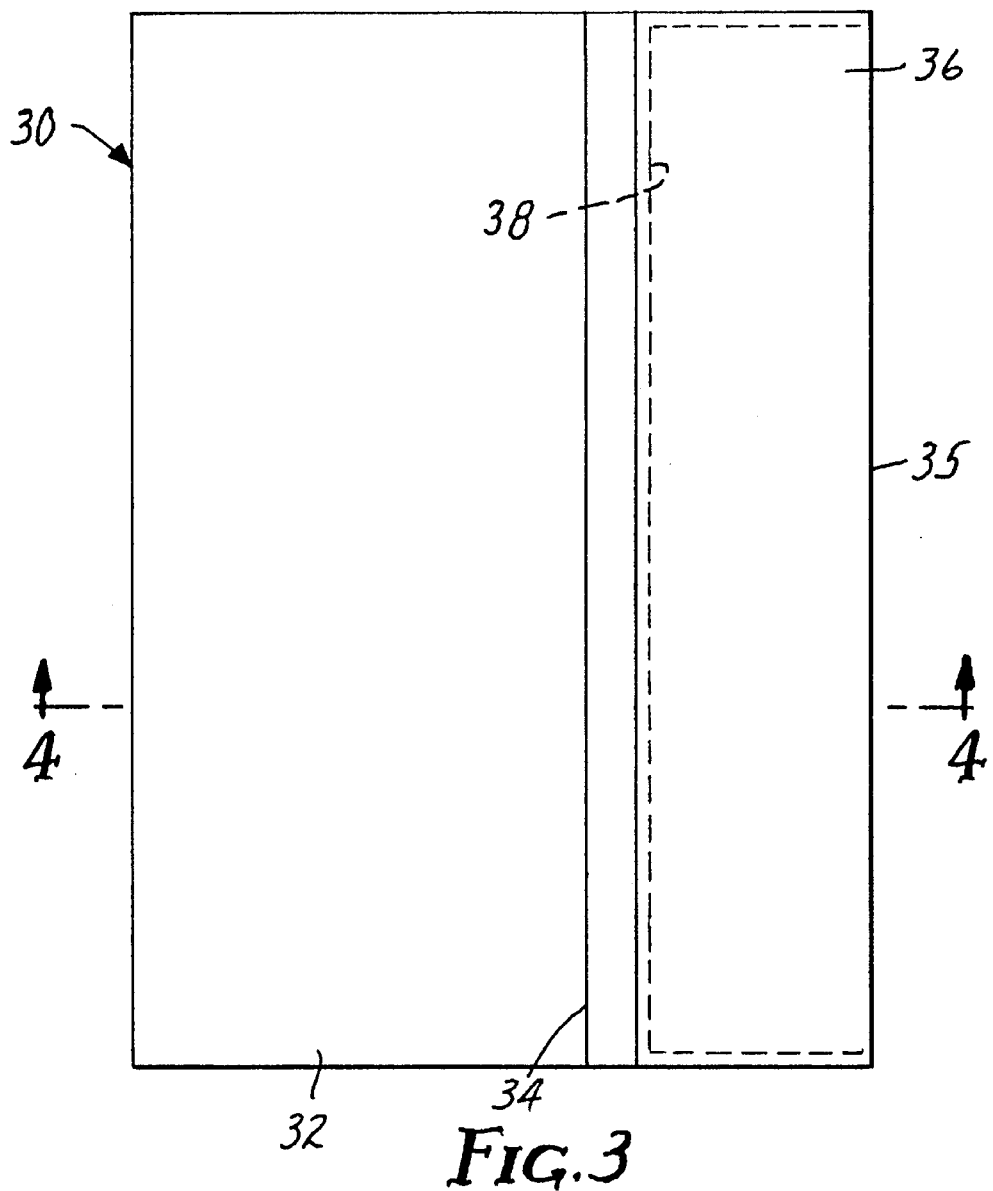
FIG. 3 is a plan view of an alternative embodiment of the present invention, with the adhesive defining the cavity shown in phantom.

FIG. 3 shows a plan view of an alternative embodiment 30 of the present invention, wherein paper substrate sheet 32 is provided with a coating of volatile liquid containment treatment 34 at a portion of the substrate. Substrate sheet 32 is folded over to define the cavity, together with adhesive 38 shown in phantom.

Figure 4:
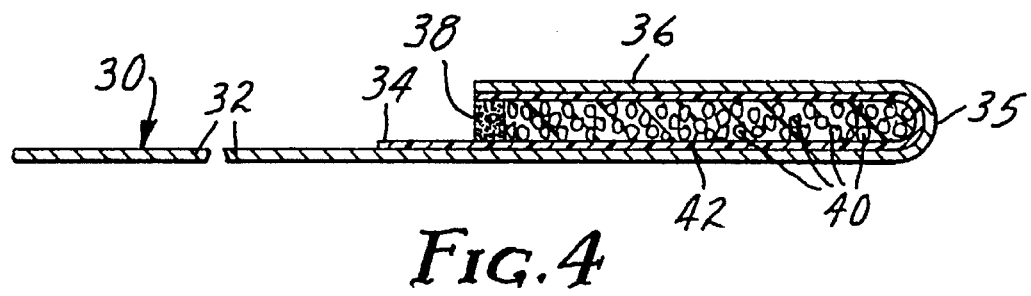
FIG. 4 is an enlarged cross-sectional view of the embodiment shown in FIG. 3 taken along line 4—4.

FIG. 4 is a cross sectional view of the embodiment shown in FIG. 3 taken along line 4—4. Paper substrate sheet 32 having liquid containment treatment 34 is folded over at line 35 to form a cover portion 36. Cover portion 36 is adhered to paper substrate sheet 32 with adhesive 38, thus defining a cavity having microcapsules 40 disposed therein. Optional binder 42 adheres microcapsules 40 to paper substrate sheet 32.

Figure 5:
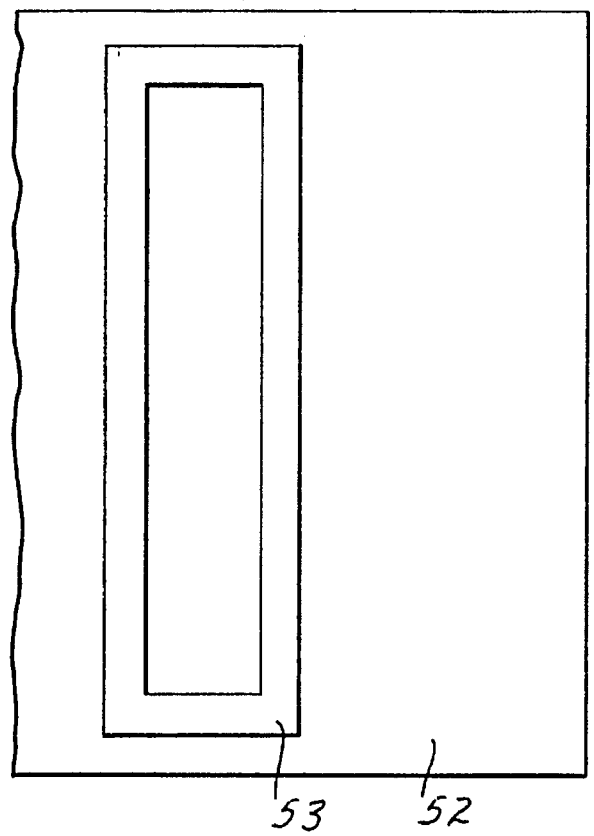

FIGS. 5–12 are sequential representations of steps in preparing a preferred embodiment of the present invention. FIG. 5 is a plan view of the first step of this preparation, wherein release coating 53 is applied to a predetermined zone on paper substrate sheet 52. Release coating 53 may be any material that preferentially causes adhesive failure in adhesion of paper substrate sheet 52 to another piece of paper through an adhesive. This adhesive failure may be due to low surface energy of the surface as may be experienced in traditional low adhesion backsize material such as silicone treatments or perfluorinated treatments or using other materials that the adhesive does not adhere well to, such as heat-set inks or varnishes. Alternatively, the preferential adhesive failure may be due to internal fracturing of release coating 53 due to poor internal cohesion of this layer.

Figure 6:
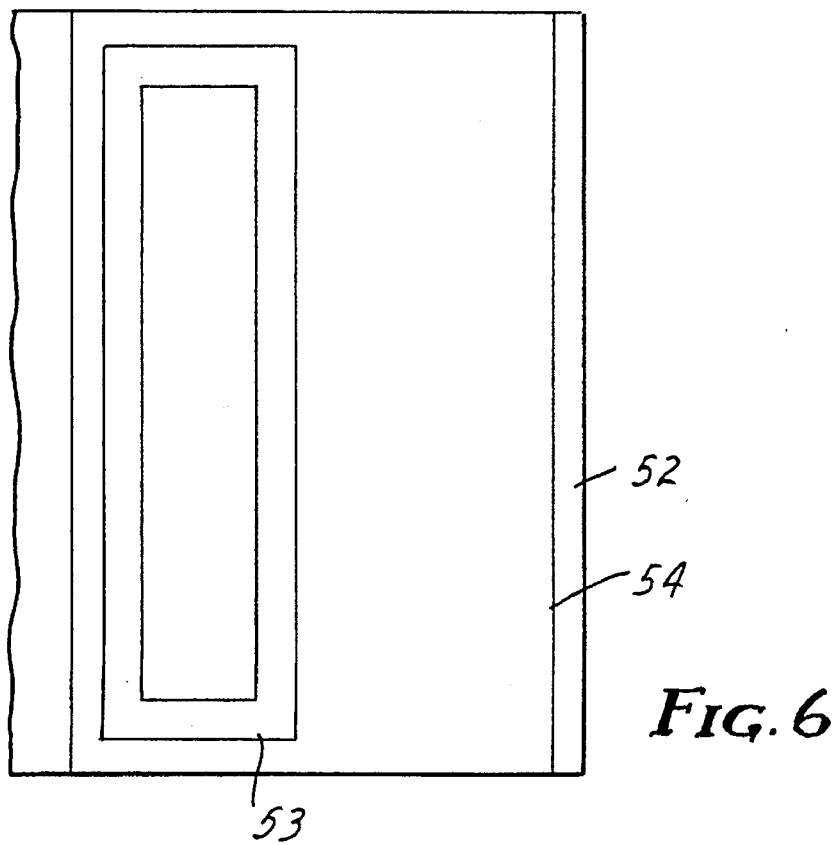

FIG. 6 shows the next step in the method of preparing the embodiment of the present invention, wherein paper substrate sheet 52 and release coating 53 are treated with volatile liquid containment treatment 54. Preferably, this volatile liquid containment treatment is a polyvinyl alcohol containing a crosslinking agent. This coating is dried and crosslinked in a second oven.

Figure 7:
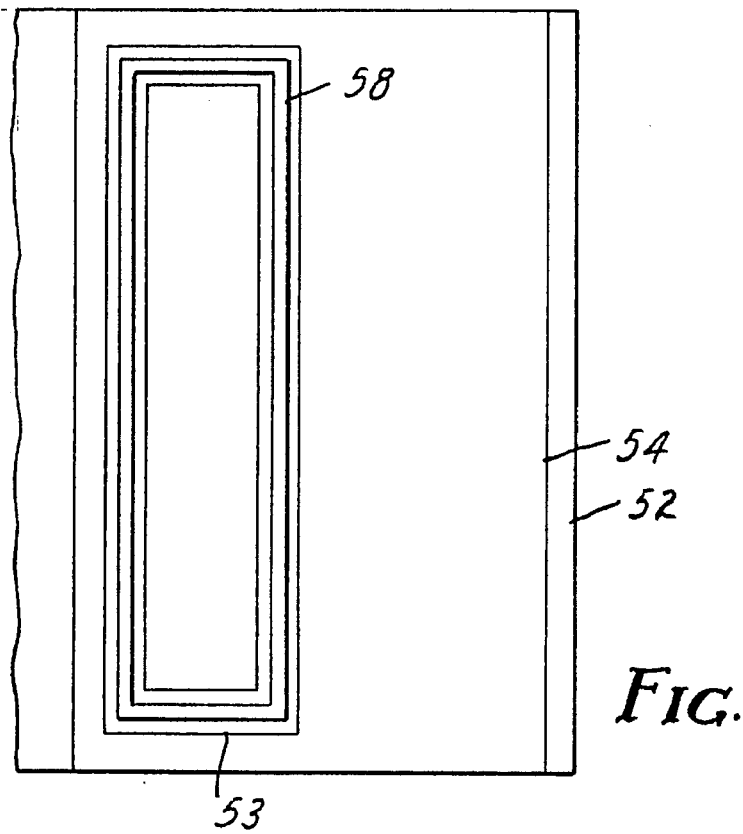
Figure 8:
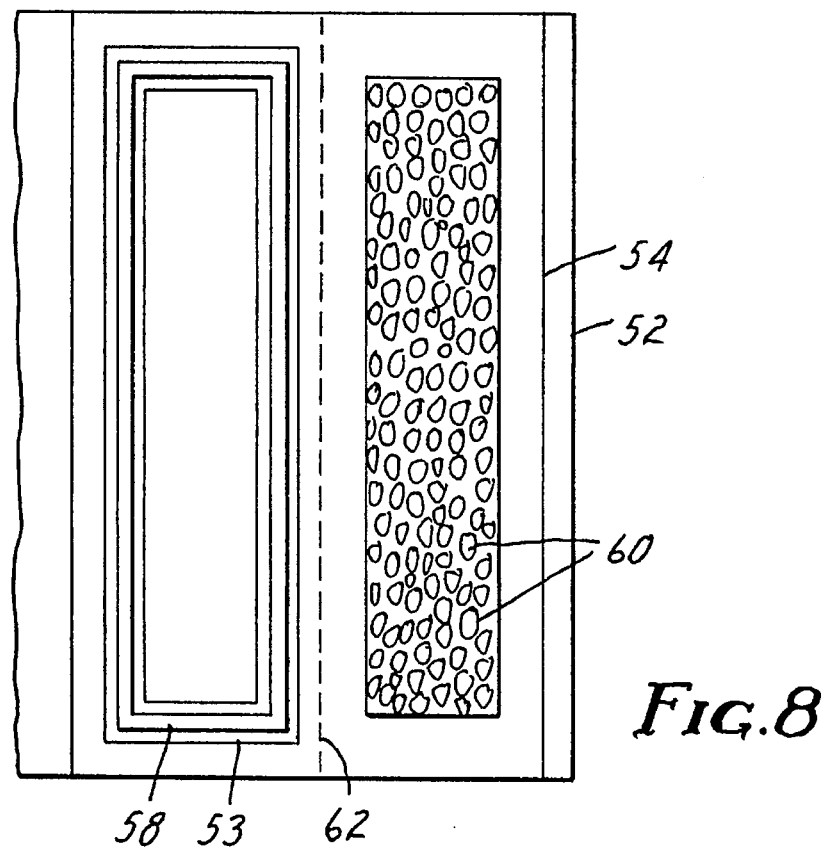
Figure 9:
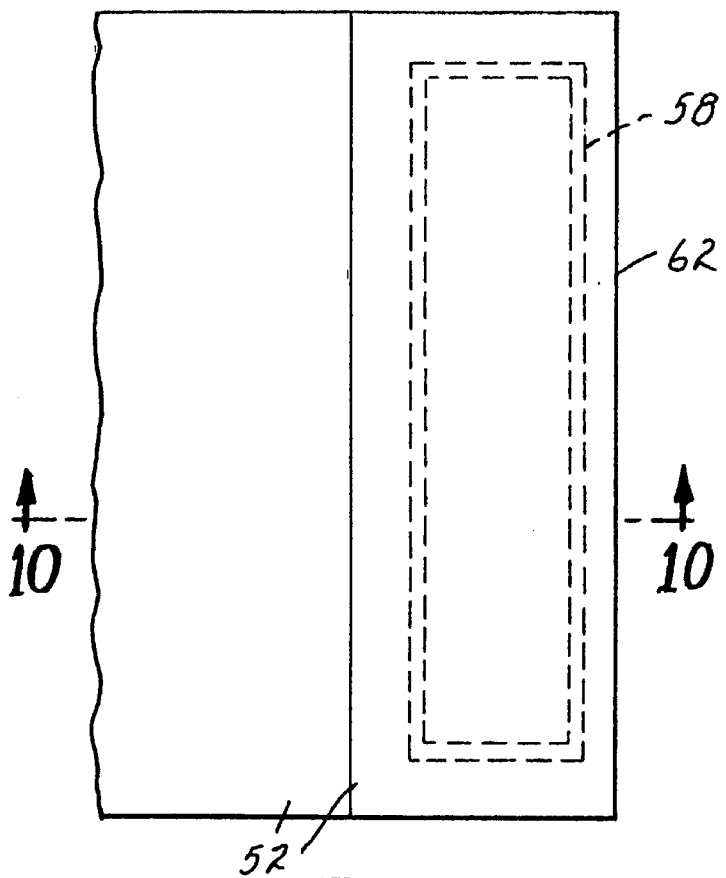
Figure 10:
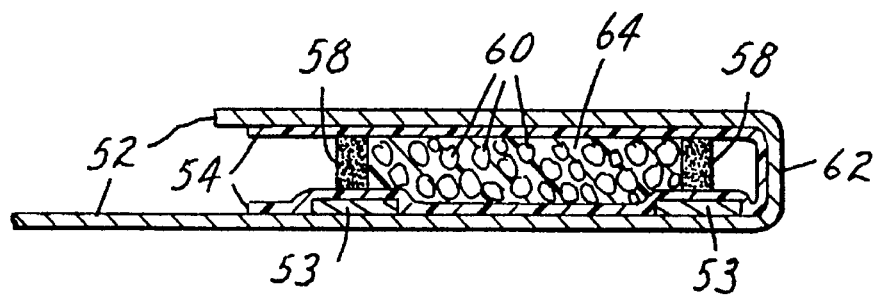
Figure 11:
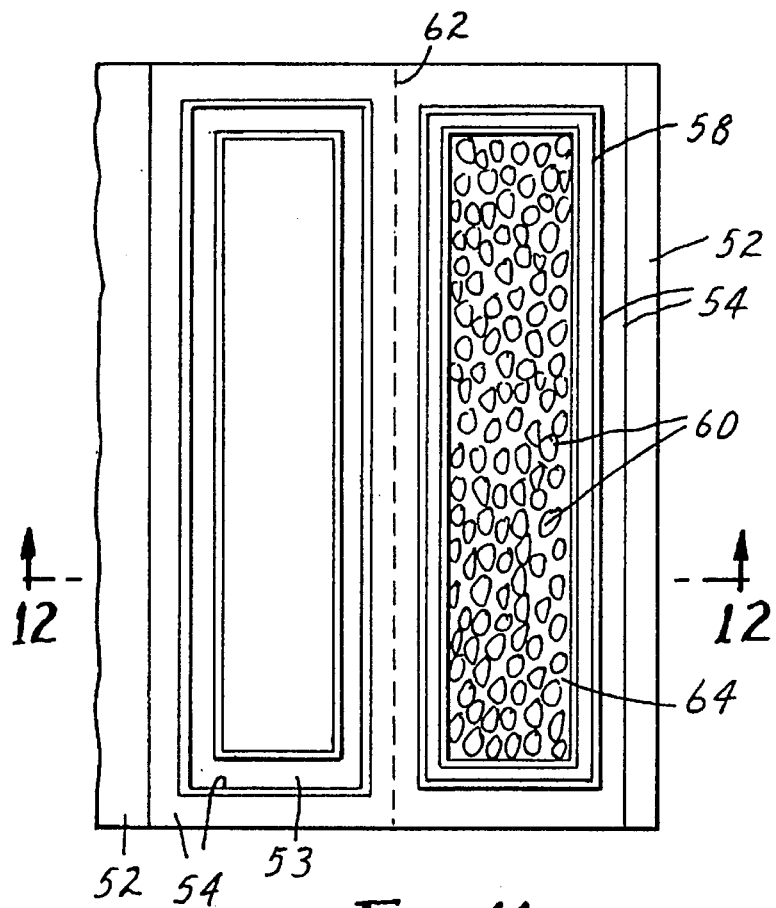
Figure 12:
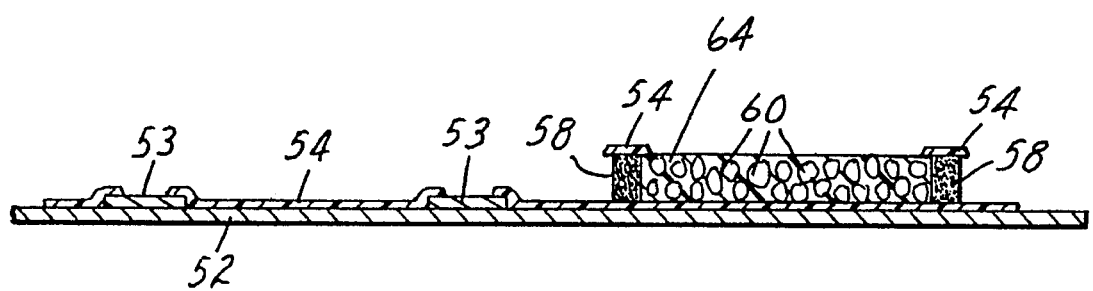

FIG. 7 represents the next step in preparing the preferred embodiment, which comprises placing adhesive 58, such as a standard envelope glue, in a pattern over the area previously coated by release coating 53. In the next step, as represented in FIG. 8, microcapsules 60 are provided in an area spaced from the region defined by adhesive 58, and on top of volatile liquid containment treatment 54. The embodiment as shown in FIG. 8 is folded at fold line 62 to form a fully enclosed cavity as shown in FIG. 9, with adhesive 58 shown in phantom. A cross sectional view of the embodiment shown in FIG. 9 is taken along line 10—10 is shown in FIG. 10. As represented in cross-sectional view of FIG. 10, capsules 60 are lightly bound to volatile liquid containment treatment 54 by binder 64. When this embodiment is opened to sample the fragrance, adhesive 58 is transferred to the portion of paper substrate 52 on the opposite side of fold line 62 from release coating 53. This result is shown in FIG. 11, and in the cross sectional view of FIG. 12, taken along line 12—12. Volatile liquid containment treatment 54 splits away from release coating 53, thereby providing easy opening of the embodiment without paper fiber delamination or tearing. This provides an attractive piece both in the closed and open position of the sampler.

The volatile liquid containment treatment of this invention is selected to be water-insoluble after cure, and insoluble in the selected organic liquid capsule fill that is to be used in the particular embodiment to be constructed.

The volatile liquid containment treatment is a polymeric material that may be coated at rapid web speed from an organic solvent or water, and which forms an effective barrier to oil and water fluids that migrate through the paper and to be sensed by persons handling the sampler or magazines containing the sampler. Preferably, the volatile liquid containment treatment is impervious to liquids, but allows the transmission of moisture vapor through the layer. Preferably, the polymer is chemically cross-linked in situ. Alternatively, the polymer may derive its barrier properties from "virtual crosslinks" that are achieved through strong interchain attractive forces such as polymer chain entanglement, ionic interactions, crystallization, van der Walls forces and hydrogen bonding. Entanglement of polymer chains, for example, would likely be observed in block copolymers containing highly phase separated domains. Similarly, polymers containing significant ionic species have strong polar interactions that will provide an effective barrier to liquids, and thus act as a volatile liquid containment treatment under this invention. Chemically crosslinked polymers that are crosslinked in situ are the preferred volatile liquid containment treatment material.

In accordance with this invention, the volatile liquid containment treatment may be applied to a paper substrate at a high web speed and at very low cost. No additional adhesives or expensive lamination techniques are required to achieve the desired containment of volatile liquids.

Preferably, the volatile liquid containment treatment is transparent, so that the underlying ink is not distorted to the naked eye through the treatment layer.

The volatile liquid containment treatment polymer preferably is cast from an appropriate system that will not damage the image created by any ink that may underlie the portion of the paper to be treated. Thus, when the ink is solvent sensitive, the volatile liquid containment treatment must be cast only from solvents that will not dissolve or adversely affect the ink in the time required for the carrier to dissipate. Because most standard and economical press inks are water insoluble, the protective polymer treatment preferably is cast from a water system, either a water solution or emulsion based. Water systems also are advantageous because they do not contain significant quantities of volatile organic components that may have an adverse ecological effect.

Polymers that may be selected for use in the present invention include the polyvinyl alcohols and copolymers thereof, urethanes, acrylated urethanes, acrylate functional acrylate polymers, ethylenically unsaturated monomers, styrene-butadiene polymers, Carboset resins and the like. The above polymers may be rendered suitable for use as a volatile liquid containment treatment in one or more ways. While all of the above polymers may be crosslinked by adding an appropriate crosslinking agent to the solution before application to the paper, alternative curing methods may be utilized as will now be apparent to the skilled artisan. For example, many of the vinylic polymers may be crosslinked by exposure to electron beam or ultraviolet radiation. Alternatively, the readily crystallizable polymers, such as the polyvinyl alcohol polymers or copolymers, may be crystallized by exposure to heat to provide a protective barrier to liquids.

Ionic polymers, such as the Carboset resins commercially available from B.F. Goodrich, Inc. are preferably cast from high pH solutions. As the water evaporates and the pH decreases, the ionic attractions of the polymers promote formation of a volatile liquid containment treatment that is impermeable to water and organic liquid capsule fill.

Crosslinked polyvinyl alcohol is well suited as the volatile liquid containment treatment of this invention as it is both readily applied from aqueous solution and crosslinked by a number of commercially available agents. Cross-linking agents may be selected from those components known in the art to effect crosslinking of the polymer to make the volatile liquid containment treatment. Examples of such crosslinkers useful for polyvinyl alcohol polymers are dimethylolurea, trimethylolurea, glyoxal, glutaraldehyde, oxalic acid, diepoxides, polyacrolein, dialdehyde starch, divinyl sulfone, diisocyanates, dihydroxydiphenylsulfone, various organometallic compounds such as the titanates commercially available under the KEN-REACT Brand from Kenrich Petrochemicals, Inc., the zirconium analogs to the above titanates, and other bifunctional compounds that react with hydroxyl groups. Cross-linking rate enhancers, such as peroxy catalysts, may also be employed. Similarly, the Carboset resins may be cured by reaction with formaldehyde condensation resins, epoxy resins and multivalent metal ions such as calcium, zinc, iron or aluminum.

The polymer is preferably cross-linked in situ by first adding an effective amount of cross-linking agent to the polymer composition before application to the paper. Preferably, the polymer has a pot life of an hour to a day before application is hampered by cross-linking. The volatile liquid containment treatment may be applied to the paper using any appropriate application method, including, for example, spraying, bar coating, roll coating, extrusion coating, pad coating and curtain coating. The thus treated paper is passed through an oven to speed up the curing process of the volatile liquid containment treatment. Typically, the paper is passed through an oven such that the web temperature is between 200° and 300° F., and more preferably between 215°–250° F. at a web speed of 400–1000 feet/minute.

In use, the cross-linkable polymer is cast on the paper substrate at as low a treatment weight as possible, while still affording the desired amount of containment of volatile liquids. Generally, a treatment weight at least sufficient to avoid having void areas in the volatile liquid containment treatment is required. Treatment weights of between about 0.3 to 1.4 lb/1300 sq ft. are preferred, with treatment weights of about 0.5 to 0.9 lb/1300 sq ft. being particularly preferred.

The adhesive that may be used to adhere the treated paper sheet(s) together to form the enclosed cavity may be selected from any of the adhesives known in the art, including pressure-sensitive adhesives, hot melt adhesives, contact adhesives, or the like. When the adhesive is aggressive in bonding the treated paper substrates together, preferably they are used in conjunction with a release coating to preferentially separate the sheets without tearing. Alternatively, the adhesive is selected to be non-aggressive such that the adhesive bond fails before the paper substrate tears or is damaged. Adhesives may be rendered less aggressive through a non-tacky filler, including filling with fragrance-containing microcapsules. Microcapsule-containing adhesives may fail by fracture of the microcapsule, which results in delivery of the fragrance contained in the microcapsule.

An additional alternative adhesive that may be selected for adhering treated paper sheet(s) together to form the enclosed cavity is a repositionable adhesive, such as disclosed in U.S. Pat. No. 3,691,140 to Silver. In this embodiment, the sampler could be opened without damage to the paper sheet(s), the fragrance sampled and the sampler could be reclosed for subsequent reopening to sample remaining fragrance at a later time.

The ink to be used in the present invention is preferably a standard printing ink available in the industry. Preferably, the selection of ink is matched with the selection of volatile liquid containment treatment to be used such that the combination has sufficient cohesive and adhesive strength to remain on the paper without splitting off. This is particularly important in the sampler format where the microcapsules are adhered to the substrate and cover sheet, and are ruptured upon removal of the cover sheet. Cohesive or adhesive failure of the underlying ink in this format could result in absolute failure of delivery of the fragrance.

The binder material used for adhering the microcapsules to the substrate paper, or the cover paper to the substrate paper may be any appropriate pressure sensitive, water or solvent soluble, or thermally activatable adhesive. Appropriate materials include polyurethanes, polyacrylates, polyvinyl resins, polyamides, polyesters, polyolefins, gum arabic, gelatin and the like. The binder material used for adhering the microcapsules to the substrate paper may optionally also act as the adhesive for adhering the cover paper to the substrate paper. There is generally no need for a gap between the fragrance-containing portion of the enclosed cavity and the adhesive that defines one of the edges of the enclosed cavity.

Alternative configurations of the microcapsules within the cavity may be utilized, depending on the desired final product. Fragrance samplers presently are provided in several alternative formats. The first format is where the cover sheet of paper is adhered to the substrate sheet of paper by a binder material provided with the microcapsules. In this format, the microcapsules are strongly bonded to the paper, so that when the cover sheet is removed from the substrate sheet, the microcapsules are ruptured and the fragrance is released. In a second format, the microcapsules are loosely associated with the substrate sheet, and when the cover sheet is removed, the microcapsules are available to be picked up by the user and applied to any location, usually by the finger. In yet another format, the microcapsules are lightly bound to the substrate sheet by a binder material, and may be removed by light finger pressure. An additional format is a combination of one or more of the above, where the user receives an initial burst of fragrance upon removal of the cover sheet and rupture of the bound microcapsules and is still able to pick up microcapsules from the paper to apply to any desired location.

In addition to microcapsules being disposed within the enclosed cavity, other sources of fragrance may be provided in the present sampler. For example, free fragrance oil or materials that deliver fragrance oil in a manner other than through traditional encapsulation may be provided together with the microcapsules for enhanced fragrance delivery. An example of an alternative means for delivering fragrance oil is by adsorbing the fragrance oil on particles. Preferably, the particles have a large amount of surface area to provide sites for absorbing the fragrance oil. An example of such a particle is talc. Another example of particles with a large amount of surface area are polymeric particles formed in the presence of incompatible materials that are later removed to provide particles having interstices to take up fragrance oil. Alternatively, the polymer of the particle may be selected such that it is swollen by the fragrance oil, thereby acting as a vehicle for delivery of fragrance oil from a device of the present invention.

In a typical manufacturing operation, the paper is first printed with the ink as desired. The ink is then dried in-line by passing through an oven. Volatile liquid containment treatment is then applied to the paper, and allowed to cure as appropriate for the material selected. Curing may optionally be accelerated by passing the paper through a second oven. Optional anchoring layers for anchoring the microcapsules to the substrate may be applied and dried at this point. Microcapsules are then applied to the paper, preferably in a water-based slurry. A treated cover sheet is then provided over the microcapsules. The cover sheet may be a separate paper, or may be provided by folding over of the substrate sheet to overlie the microcapsules. It has been found that an additional drying step is not usually required at this stage to prepare a satisfactory product.

The following examples are provided for purposes of illustration only, and are not intended to be limiting of the scope of the invention in any way.

EXAMPLE 1

In the following example, a fragrance oil was encapsulated by the process described in Example 20 of U.S. Pat. No. 3,516,941. The resulting capsules had a mean diameter of about 20 micrometers and an estimated payload of 85% by volume (ratio of oil to total capsule volume.) The microcapsules were washed with cold tap water, filtered, and reslurried to 40% solids.

| Component | Dry Weight | Wet Weight |
| --- | --- | --- |
| Microcapsules (40% solids) | 1215.50 | 3038.75 |
| Klucel MF (added as a 3.3% predissolved solution) | 6.50 | 197.00 |
| Superpearl (pearlescent pigment obtained from Flamenco) | 78.0 | 78.0 |

This mixture was diluted with water to 36.7% solids, with a resulting viscosity of 700 cps. The slurry was thoroughly mixed and passed through a 125 micron screen to remove large particles or agglomerates.

The volatile liquid containment treatment (PVA treatment) solution was prepared by predissolving the Airvol 523 in water to 14% solids. The glyoxal, ammonium chloride and water were added and thoroughly mixed just prior to coating.

| Component | Dry Weight | Wet Weight |
| --- | --- | --- |
| Airvol 523 polyvinyl alcohol | 812.25 | 5801.8 |
| Glyoxal | 97.85 | 244.6 |
| Ammonium chloride | 40.00 | 40.00 |
| Water | 950.10 | 6086.4 |
|  |  | 890.26 |
|  | 332.13 | 3016.27 |

Samplers were produced at Japs Olson Printing Co. on their M-80-5 Harris heat set web off-set printing press at a speed of 200 feet per minute. The Warrenflo 70 pound C2S paper was printed with varnish (Arroweb HS Oraprint high gloss varnish) and dried in the first oven. The PVA treatment described above was applied over the printing just prior to a second oven at a variety of treatment weights from 0.60 to 1.40 pounds per 1300 square feet. The treatment was dried and crosslinked at a web temperature of 235° F. An adhesive perimeter of standard envelope glue (Craigbond 3822P water-based business form adhesive) was applied over the varnish and PVA treatment. The microcapsule/pigment slurry was then coated over the crosslinked polyvinyl alcohol at 3.5 pounds per 1300 square feet as shown in FIG. 8. The paper was folded so that a treated portion of the paper covered the microcapsules, and was allowed to dry at ambient conditions for 72 hours. After drying and opening the sample, the microcapsules could easily be removed for application to the skin by rubbing with a finger tip.

The reduction in detectable volatile organic liquid capsule fill material after crushing of the microcapsules without opening of the sampler was evaluated using gas chromatography as follows.

FRAGRANCE EMISSION RATIO TEST

The sample is triggered by pinch rolling the sampler once on each side, leaving an uncrushed margin at each end to avoid extruding the capsule fill material through the end of the sampler.

Two crushed unopened samples are immediately placed in a container provided with an inlet and an outlet to allow purging of the container with nitrogen. An SKC charcoal cartridge (Cat. No. 226-01, SKC Inc., Eighty Four, Pa.) for collection of volatile organic components is installed between the sample-containing box and a flowrator. The box is purged with nitrogen for ½ hr. at 200 ml/min. flow rate. The nitrogen is shut off, the cartridge is opened and the front end charcoal is carefully emptied into a gas chromatograph sample vial containing 1 µl of decyl acetate internal standard. 1 ml of carbon disulfide is added and the vial is capped, shaken briefly and analyzed by gas chromatography to determine amounts of volatile organic components isolated.

The gas chromatograph is temperature programmed to increase from 50° to 300° C. at 5°/min. The column used is a boiling-point column (Restek $Rt_x$-1, cross-linked PDMS capillary, 30 m×0.32 mm id, 0.25 µm df), 50/1 split ration, injector/detector temps 320° C. The standard is 4 µl of oil in 1 ml of acetone, hexane, or methanol, with a 4 µl injection. Attenuation may be 2(1/100) for standard, 0(1/1) for samples.

The results of this test are reported in Table I below as a ratio of amount of fragrance collected in the gas chromatograph as compared to the standard described above. Because the amount of capsule fill present in the box from two samples should be the same for all experiments, this test is believed to be a good comparison of relative containment of fragrance. Some variation due to experimental condition differences is expected if differing amounts of capsules are fractured in the pinch rolling step.

TABLE I

| Containment Treatment Coating Wt. lbs/1300 Ft[2] | Test 1[1] | Test 2[2] | Test 3[3] | Test 4[4] | Test 5[5] | Test 6[6] |
|---|---|---|---|---|---|---|
| 0.60 | 4.97 | 4.78 | 1.39 | 0.00 | 23.99 | 0 |
| 0.80 | 3.26 | 2.64 | 2.10 | 1.89 | 64.26 | 15.57 |
| 1.00 | 3.87 | 3.19 | 1.13 | 0.91 | 49.57 | 17.81 |
| 1.20 | 2.25 | 1.20 | 3.55 | 2.80 | 48.64 | 19.22 |
| 1.40 | 3.05 | 1.40 | 2.80 | 2.14 | 29.83 | 4.93 |
| 0.00 | 25.21 | 13.54 | 0.00 | 0.00 | 0.00 | 0.00 |

[1] Test 1 represents the percent of fragrance leaking through the paper. Analysis run at time zero after crushing the capsules. Average of five analyses.
[2] Test 2 represents a certain component (at time about 13 min.) leaking through the paper. Analysis run at time zero after crushing the capsules. Average of five analyses. If comparing the amount of leakage on a sample with no barrier coat to a sample with, for example, 1.2 lbs. barrier coat, the amount of leakage has been reduced by 25.21 ÷ 2.25 = 11.2 times.
[3] Test 3 is analysis of same samples as 1 but after they aged for 168 hours after crushing the capsules. Average of five analyses.
[4] Test 4 is analysis of same samples as 2 but after they aged for 168 hours after crushing the capsules. In the sample having no barrier coat, all the fragrance that could be detected by the G.C. has evaporated. Samples having a barrier coating still show leakage, indicating that the fragrance is trapped inside the unit.
[5] Test 5 is analysis of same sample as 1 but the sample has been opened to allow all fragrance inside to be detected by the G.C. One analysis only.
[6] Test 6 is analysis of same sample as 2 but the sample has been opened to allow all fragrance inside to be detected by the G.C. One analysis only.

The fragrance in the sample with no barrier coat had all evaporated while it was sealed. All the other samples, which are sealed samples with barrier coat, show a great deal of fragrance still contained in the samples. In other words, the fragrance was trapped inside the unit and could not evaporate through the barrier coat. There was also free oil evidence on samples having a barrier coat, while no free oil was evident on samples having no barrier coat.

Preferably, the amount of fragrance released by the sampler of the present invention emits less than one-fifth of the fragrance released by a sampler having no volatile liquid containment treatment as compared using the above described FRAGRANCE EMISSION RATIO TEST. More preferably, the amount of fragrance released by the sampler of the present invention emits less than one-eighth of the fragrance released by a sampler having no volatile liquid containment treatment as compared using this test.

What is claimed is:

1. A method of making a sampler for delivery of microencapsulated liquid fragrance material comprising
   a) printing a substrate sheet with release coating,
   b) applying a volatile liquid containment treatment which, when cured, is an organic polymer, to said substrate sheet and overlying at least a portion of said release coating,
   c) allowing said volatile liquid containment treatment to cure to a state so that it is liquid water-stable and organic liquid capsule fill-stable such that said substrate sheet having volatile liquid containment treatment thereon allows the transmission of water moisture vapor therethrough,
   d) applying an adhesive generally overlying the area corresponding to the release coating and overlying at least a portion of said volatile liquid containment treatment,
   e) applying microcapsules comprising microencapsulated organic liquid capsule fill to said substrate sheet such that they are disposed on at least a portion of the volatile liquid containment treatment,
   f) folding said substrate sheet so that the adhesive and portions of the substrate sheet define an enclosed cavity having said microcapsules disposed therein.

2. The method of claim 1, wherein said adhesive additionally contains microcapsules that comprise microencapsulated organic liquid capsule fill.

3. The method of claim 1, wherein said organic liquid capsule fill is a fragrance.

4. The method of claim 1, wherein said cured volatile liquid containment treatment is a crosslinked polymer.

5. The method of claim 1, wherein said microcapsules are strongly bonded to said substrate paper sheet by a binder, so that when the said cavity is opened the microcapsules are ruptured and the fragrance is released.

6. The method of claim 1, wherein said microcapsules are loosely associated with the substrate sheet, such that when the cavity is opened the microcapsules are available to be picked up by a user.

7. The method of claim 1, wherein said microcapsules are lightly bound to the substrate sheet by a binder material, such that when the cavity is opened the microcapsules may be removed by light finger pressure.

8. The method of claim 1, wherein said volatile liquid containment treatment is provided at a treatment weight between about 0.3 lb/1300 sq. ft. and 1.4 lb/1300 sq. ft.

9. The method of claim 1, wherein said volatile liquid containment treatment is provided at a treatment weight between about 0.5 lb/1300 sq. ft. and 0.9 lb/1300 sq. ft.

10. The method of claim 1, wherein said cured volatile liquid containment treatment is a crosslinked polyvinyl alcohol polymer.

11. The method of claim 1, additionally comprising free fragrance oil disposed within said enclosed cavity.

12. The method of claim 1, additionally comprising a particle disposed within said enclosed cavity, wherein said particle has fragrance oil adsorbed therein.

13. The method of claim 1, additionally comprising a particle disposed within said enclosed cavity, wherein said particle is a polymeric particle that is swollen by fragrance oil.

* * * * *